United States Patent [19]

Vincent et al.

[11] Patent Number: 5,266,576
[45] Date of Patent: Nov. 30, 1993

[54] N-MYRISTOYL TRANSFERASE INHIBITORS

[75] Inventors: Michel Vincent, Bagneux; Georges Remond, Versailles; Bernard Portevin, Elancourt; Jean-Albert Boutin, Suresnes, all of France; Ghanem Atassi, Saint-Cloud, Belgium

[73] Assignee: Adir et Compagnie, Courbevoie, France

[21] Appl. No.: 833,301

[22] Filed: Feb. 10, 1992

[30] Foreign Application Priority Data

Feb. 11, 1991 [FR] France .................. 91 01502

[51] Int. Cl.$^5$ .................. A61K 31/44; A61K 31/40; A61K 31/415; C07D 471/04
[52] U.S. Cl. .................. 514/300; 514/397; 514/400; 514/415; 546/121; 546/208; 546/210; 546/226; 548/496; 548/540; 548/314.7; 548/311.1; 548/338.1; 548/312.1; 554/112; 549/455; 544/127; 544/139; 544/176; 544/362; 544/370; 544/373; 544/399
[58] Field of Search .............. 514/559, 300, 397, 400, 514/415; 554/112; 546/121, 208, 210, 226; 544/127, 139, 176, 362, 370, 373, 399; 548/342, 496, 540; 549/455

[56] References Cited

U.S. PATENT DOCUMENTS 5,164,414 11/1992 Vincent et al. .................. 514/563

Primary Examiner—C. Warren Ivy
Assistant Examiner—D. Margaret Mach
Attorney, Agent, or Firm—Gordon W. Hueschen

[57] ABSTRACT

The invention relates to a compound of formula (I):

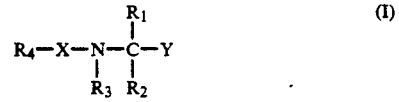

which can be used as N-myristoyltransferase inhibitors, in which $R_1$ represents hydrogen, substituted or unsubstituted ($C_1$-$C_6$) alkyl, substituted or unsubstituted phenyl, ($C_3$-$C_7$) cycloalkyl methyl, substituted or unsubstituted (imidazolyl-2-yl)methyl, substituted or unsubstituted (indol-3-yl)methyl or (1-azaindolizin-2-yl)methyl, $R_2$, $R_3$, which are identical or different, represent hydrogen or (Cl-C6) alkyl, or when $R_1$ represents hydrogen, $R_2$ and $R_3$ form with the carbon and nitrogen atoms to which they are attached, a mono-, bi- or tricyclic heterocycle, X represents —CO—, —SO$_2$—, —PO(OH)—, Y represents —COR$_5$ or —POR$_6$R$_6'$, $R_4$ represents substituted or unsubstituted, linear or branched ($C_6$-$C_{21}$) alkyl in which, depending on the individual case, one or more methylene may be replaced by oxygen or sulfur or by a p-phenylene ring, their isomers, diastereoisomers and epimers as well as their addition salts with a pharmaceutically acceptable acid or base.

4 Claims, No Drawings

N-MYRISTOYL TRANSFERASE INHIBITORS

The subject of the present invention is new N-myristoyltransferase inhibitors.

It is known from the prior art that the N-terminal amino group of proteins is blocked by acetyl, pyroglutamyl and formyl groups. However, SHOJI et al. have demonstrated that myristic acid was attached by a covalent bond to the N-terminal group of the catalytic subunits of cyclic AMP dependent protein kinase (Proc. Natl. Acad. Sci. USA, (1982), 79, 6123–6131).

The existence of this terminal myristoyl group has since been shown in various other proteins such as calcineurin B (AITKEN et al., Febs Letters, (1982), 150, No. 2, 314–318) or tyrosine protein kinase (TPK) (BUSS and SEFTON, J. Virol, (1985), 53, 7–12).

Also in the area of oncogenes, BISHOP has identified that a transforming protein underwent myristoylation during maturation. It has, furthermore, been shown since that this maturation stage involving myristoylation was essential for the transforming power of this protein (KAMPS, BUSS and SEFTON, Proe. Natl. Acad. Sci. USA, (1985), 82, 4625–4628). This concept has since been generalized to many other transforming proteins of viral origin (RHEE and HUNTER, J. Virol., (1987), 61, 1045–1053). This maturation is catalyzed by an enzyme called N-myristoyltransferase (NMT) identified in yeast by TOWLER and GLASER (Proc. Natl. Acad. Sci. USA, (1986), 83, 2812–2816).

However, NMT practically recognizes, as cosubstrate, only myristic acid on the one hand and, on the other hand, as substrate, the proteins comprising a glycine as the last amino acid on the N-terminal side, with the participation of the peptide sequence contiguous to this glycine (participation of 7 amino acids).

Thus, the myristoylation of the N-terminal glycine residue of some proteins plays a very important role in some mechanisms involved in the transformation of cells and in the control of their proliferation. Furthermore, it has been shown by SHOJI et al. (Japanese Patent JP 63,146,851, JP 62,255,810 and JP 62,126,384) that myristoylglycine or oligopeptide derivatives possessed an inhibitory effect against cell transformation or proliferation or retrovirus multiplication.

The invention relates more specifically to the compounds of formula (I)

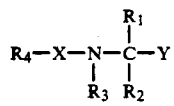

in which $R_1$ represents
a hydrogen atom,
a linear or branched ($C_1$-$C_6$) alkyl group which is unsubstituted or substituted by one or more hydroxyl, amino, carboxyl, carbamoyl, benzylthio, methylthio, mercapto groups or a phenyl group (unsubstituted or substituted by one or more halogen atoms or hydroxyl, linear or branched ($C_1$-$C_6$) alkyl, linear or branched ($C_1$-$C_6$) alkoxy or ($CH_3$—$CH_2$—O)$_2$PO—$CH_2$—groups),
a phenyl group which is unsubstituted or substituted by one or more halogen atoms or hydroxyl or linear or branched ($C_1$-$C_6$) alkyl groups,
a ($C_3$-$C_7$) cycloalkyl methyl group,
an (imidazol-2-yl)methyl group or an (indol-3-yl)methyl group which is unsubstituted or substituted on the heterocycle by a benzyl, benzhydryl, trityl, benzyloxymethyl, tosyl, linear or branched ($C_1$-$C_6$) alkyl or phenyl group,
a (1-azaindolizin-2-yl)methyl group of formula:

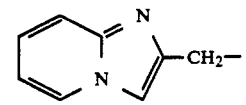

$R_2$ represents a hydrogen atom or a linear or branched ($C_1$-$C_6$) alkyl group,
$R_3$ represents a hydrogen atom or a linear or branched ($C_1$-$C_6$) alkyl group, or
when $R_1$ represents a hydrogen atom,
$R_2$ and $R_3$ may form, with the carbon and nitrogen atoms to which they are respectively attached, any one of the following heterocycles:

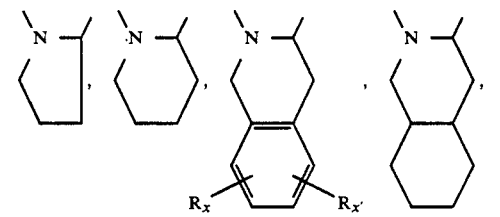

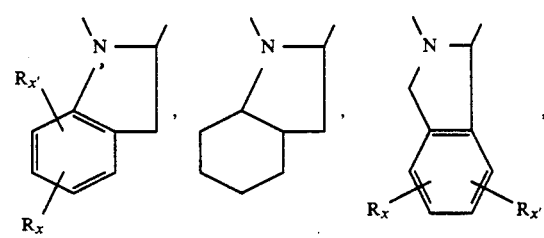

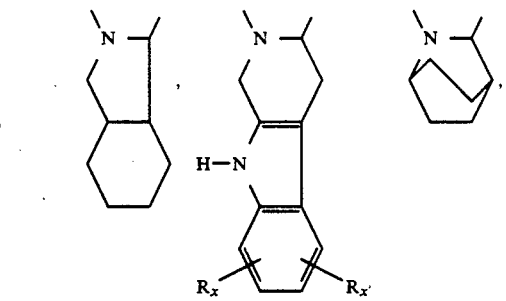

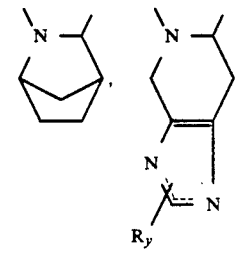

$R_x$ and $R_{x'}$, which are identical or different, represent a hydrogen atom, a linear or branched ($C_1$-$C_6$) alkyl group, a hydroxyl group, a linear or branched ($C_1$-$C_6$) alkoxy group, a halogen atom, or $R_x$ and $R_{x'}$, when they are on two adjacent carbons, form a methylenedioxy or ethylenedioxy group, $R_y$ represents a hydrogen atom, a linear or branched ($C_1$-$C_6$) alkyl group, an aryl group, an aralkyl group, an aroyl group, an arylsulfonyl group, X represents any one of the following groups:

$$-\underset{\underset{O}{\|}}{C}-,\quad -SO_2-,\quad -\underset{\underset{O}{\|}}{\overset{\overset{OH}{|}}{P}}-,$$

Y represents a $$-CO-R_5 \quad \text{or} \quad -\underset{\underset{O}{\|}}{P}\overset{R_6}{\underset{R_{6'}}{\diagdown}} \quad \text{group},$$

$R_5$ represents a hydroxyl, linear or branched ($C_1$-$C_6$) alkoxy, $H_2N-CO-CH_2-o-$, $HO-CH_2-CHOH-CH_2-O-$, $$\underset{H_3C}{\overset{H_3C}{\diagdown}}\underset{O}{\overset{O}{\diagup}}\Big]CH_2-O-,\quad \underset{R_8}{\overset{R_7}{\diagdown}}N-\text{ group},$$

$R_7$ and $R_8$, which are identical or different, represent a hydrogen atom, a linear or branched ($C_1$-$C_6$) alkyl group or form with the nitrogen atom to which they are attached, a pyrrolidine, piperidine, morpholine or piperazine ring, $R_6$ and $R_{6'}$, which are identical or different, represent a hydrogen atom, a hydroxyl or linear or branched ($C_1$-$C_6$) alkoxy group, $R_4$ represents:

1 a linear or branched alkyl group comprising 6 to 21 carbon atoms which are unsubstituted or substituted on the terminal methyl group by a hydroxyl, mercapto, phenyl or ethynyl group and in which at least one of the methylene groups is replaced by an oxygen or sulfur atom or by a p-phenylene ring, in the case where:
either $R_1$ represents—a hydrogen atom,
—a linear or branched ($C_1$14 $C_6$) alkyl group
which is unsubstituted or substituted by one or more hydroxyl, amino, carboxyl, carbamoyl, benzylthio, methylthio, mercapto groups or a phenyl group (unsubstituted or substituted by a hydroxyl group),
—an unsubstituted phenyl group,
—an (imidazol-2-yl)methyl group or an (indol-3-yl)methyl group which is unsubstituted or substituted on the heterocycle by a methyl group and $R_2 = H, R_3 = H, X = -\underset{\underset{O}{\|}}{C}-, Y = CO\ R_{5'}\ (R_{5'} = OH, \text{alkoxy})$ or $R_2$ and $R_3$ form with the carbon and nitrogen atoms to which they are attached, a proline ring and $R_1 = H, X = -\underset{\underset{O}{\|}}{C}-, Y = -CO-R_{5'}\ (R_{5'} = OH, \text{alkoxy})$ 2 in the other cases: a linear or branched alkyl group comprising 6 to 21 carbon atoms, which is unsubstituted or substituted on the terminal methyl group by a hydroxyl, mercapto, phenyl or ethynyl group and in which one or more methylene groups may be replaced by an oxygen or sulfur atom or by a p-phenylene ring, their isomers, diastereoisomers and epimers as well as their addition salts to a pharmaceutically acceptable acid or base.

Among the acids which are pharmaceutically acceptable, there may be mentioned with no limitation being implied, hydrochloric, sulfuric, tartaric, maleic, fumaric, oxalic, methanesulfonic, camphoric acids and the like.

Among the bases which are pharmaceutically acceptable, there may be mentioned with no limitation being implied, sodium hydroxide, potassium hydroxide, terbutylamine and the like.

The invention also relates to the process for preparing the compounds of formula (I) wherein: 1/ in the case where the derivatives of formula (I) which it is wished to obtain possess an $R_4 = R_{4'}$ radical in which no methylene group is replaced by a sulfur or oxygen atom, there is condensed a compound of formula (II):

$$R_{4'}-X'-Z \tag{II}$$

in which:

$$X'\ \text{represents a group}\ -\underset{\underset{O}{\|}}{C}-,\ -SO_2-,\ -\underset{\underset{O}{\|}}{\overset{\overset{O-CH_2-C_6H_5}{|}}{P}}-,$$

$R_{4'}$ represents a linear or branched alkyl group comprising 6 to 21 carbon atoms which is unsubstituted on substituted on the terminal methyl group by a hydroxyl, mercapto, phenyl or ethynyl group, and in which one or more methylene groups may be replaced by a p-phenylene group, represents a halogen atom, a hydroxyl group, a linear or branced ($C_c$-$C_6$) alkoxy group, an aralkoxy group, or a $$\underset{CO}{\overset{CO}{\diagdown}}\bigg]\ \text{group},$$
$O-N$ with an amine of formula (III) (in racemic or isomeric form) which is protected where appropriate:

$$\underset{R_3\ R_2}{HN-\overset{R_1}{\underset{|}{C}}-Y'} \tag{III}$$

in which $R_2$, $R_3$ and $R_4$ have the same meaning as in formula I and Y' represents a $-CO_2H$, $-CO(\text{alkoxy})$ or $-PO(\text{alkoxy})_2$ group, to give, after optional deprotection, a compound of formula (I/a), a special case for the compounds of formula (I)

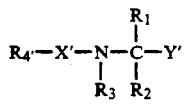  (I/a)

in which $R_1$, $R_2$, $R_3$, $R_4'$, $X'$ and $Y'$ have the same meaning as above, 2/ in the case where the derivatives of formula (I) which it is wished to obtain possess an $R_4=R_4''=CH_3-(CH_2)n$—radical in which at least one of the methylene groups is replaced by a sulfur or oxygen atom, there is condensed:

a compound of formula (IV)

  (IV)

in which:

$X'$ and $Z$ have the same meaning as above,

A represents a halogen atom, a mesyloxy group or a tosyloxy group, m is lower than or equal to n-1, and one of the methylene groups may be replaced by an oxygen or sulfur atom, a p-phenylene group, a —CH(CH$_3$)—group or a —C(CH$_3$)$_2$—group, with an amine of formula (III) (in racemic or isomeric form) which is protected where appropriate and as previously defined, to give a compound of formula (V)

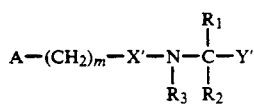  (V)

in which A, m, $X'$, $R_1$, $R_2$, $R_3$ and $Y'$ are defined as above, which is reacted with a derivative of formula (VI)

  (VI)

in which:

$R_9$ represents a $CH_3-(CH_2)p$—group which is unsubstituted or substituted on the terminal methyl group by a hydroxyl, mercapto, phenyl or ethynyl group and in which one of the methylene groups may be replaced by an oxygen or sulfur atom, a p-phenylene group, a —CH(CH$_3$)—group or a —C(CH$_3$)$_2$—group, B represents an oxygen or sulfur atom, M represents a metal chosen from sodium, potassium or cesium, p is such that the sum of m+p is lower than or equal to n−1, to give, after optional deprotection, a compound of formula (I/b), a special case for the compounds of formula (I):

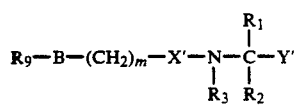  (I/b)

in which $R_9$, B, m, $X'$, $R_1$, $R_2$, $R_3$ and $Y'$ are defined as above, which derivatives of formula (I/a) and (I/b) can be written in a simplified manner:

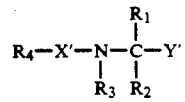  (I/a)

which a in the case where $X'$ represents

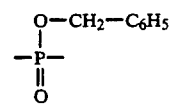

may be converted by catalytic hydrogenation into compounds of formula (I/c), a special case for the compounds of formula (I):

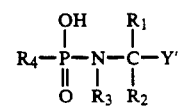  (I/c)

in which $R_1$, $R_2$, $R_3$, $R_4$ and $Y'$ have the same meaning as above, b in the case where $Y'$ represents a —CO(alkoxy) or —PO(alkoxy)$_2$ group, may be saponified completely or partially to give respectively the compounds of formulae (I/d), (I/e) and (I/f), a special case for the compounds of formula (I):

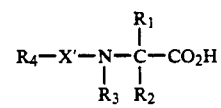  (I/d)

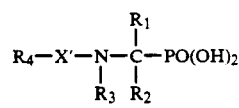  (I/e)

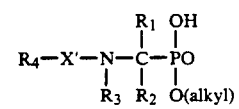  (I/f)

in which $R_1$, $R_2$, $R_3$, $R_4$ and $X'$ have the same meaning as above, c in the case where $Y'$ represents a —CO$_2$H group, may be converted in the presence of cesium carbonate using chloroacetamide, into a compound of formula (I/g), a special case for the compounds of formula (I):

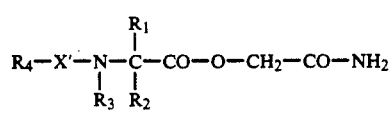  (I/g)

in which $R_1$, $R_2$, $R_3$, $R_4$ and $X'$ have the same meaning as above, d in the case where $Y'$ represents a —CO$_2$H group, may be esterified using isopropylidene glycerol, into a compound of formula (I/h), a special case for the compounds of formula (I),

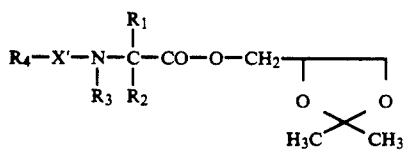

in which $R_1$, $R_2$, $R_3$ and $R_4$ have the same meaning as above, which derivative of formula (I/h) may be hydrolyzed in an acid medium to give the compound of formula (I/i), a special case for the compounds of formula (I)

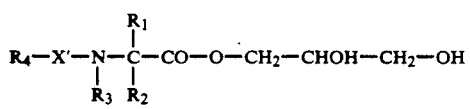

in which $R_1$, $R_2$, $R_3$ and $R_4$ have the same meaning as above, which compounds of formulae (I/a) to (I/i) may be purified, where appropriate, by a conventional purification technique, the isomers of which may be separated using a conventional separation technique, and which may be converted to their addition salts with a pharmaceutically acceptable acid or base.

In addition to being new, the compounds of formula (I) possess very advantageous pharmacological properties.

They are potent inhibitors of the myristoylation of proteins such as gag by means of the enzyme responsible for this myristoylation, that is N-myristoyltransferase (NMT).

However, NMT is localized in numerous biological sources; it can be either of cytosolic origin or of microsomal origin as has been shown by J.A. BOUTIN et al. (Biochemical Journal, 1990, submitted). The microsomal enzyme recognizes numerous endogenous proteins, oncogene products or virus structural proteins. The cytosolic enzyme, for its part, recognizes the endogenous proteins to a lesser extent.

However the compounds of the invention are not only recognized by the microsomal enzyme, but also by the cytosolic enzyme. Surprisingly, they inhibit both microsomal and cytosolic activity.

The use of the compounds of the invention as NMT inhibitors leads to an inhibition of the activity of this enzyme which is considerably higher than that of the compounds described in the prior art as inhibitors of the proliferation of cancerous cells and retroviruses.

In effect, an in-depth study of the influence exerted by the compounds of the invention on cell proliferation and transformation was carried out using cancerous cells of murine origin (L1210) or of human origin (HL60). After extracting the enzyme from this biological medium and measuring its activity, it appears that the addition of the compounds of the invention strongly inhibits its activity.

Moreover, the compounds of the invention exhibit a cytotoxic activity on cultured cancerous cells such as L1210 (of murine origin) or HL60 (of human origin). This cytotoxicity proved to be substantially higher on these cells than that due to N-myristoylglycine.

Furthermore, by means of this inhibition of NMT activity, the compounds of the invention protect cultured human T lymphocyte cells (CEM) from infection by the HIV-1 virus.

Thus, this inhibition of activity is all the more advantageous since this enzyme plays a preponderant role, in particular in the maturation of the transforming proteins involved in certain cancers or of proteins which are themselves involved in virus maturation.

The compounds of the invention therefore have applications in the treatment of cancer and/or of viral diseases whose maturation involves a myristoylation, such as AIDS, herpes, hepatitis B, influenza, poliomyelitis or leukemias.

The subject of the present invention is also the pharmaceutical compositions containing, as active ingredient, a compound of general formula (I) or one of its addition salts with a pharmaceutically acceptable base, alone or in combination with one or more inert, nontoxic excipients or vehicles.

Among the pharmaceutical compositions according to the invention, there may be mentioned those which are suitable for oral, parenteral or nasal administration, simple or sugared tablets, sublingual tablets, sachets, packets, hard gelatin capsules, sublingual preparations, troches, suppositories and the like.

The dosage will vary according to the age and the weight of the patient, the nature and the severity of the disease as well as the route of administration. This can be oral, nasal, rectal or parenteral. Generally, the unit dosage ranges from between 0.1 and 100 mg per treatment of 1 to 3 doses per 24 hours.

The following examples illustrate the invention but do not limit it in any manner.

The positions of the histidine and spinacin substituents in the examples are noted in the following manner:

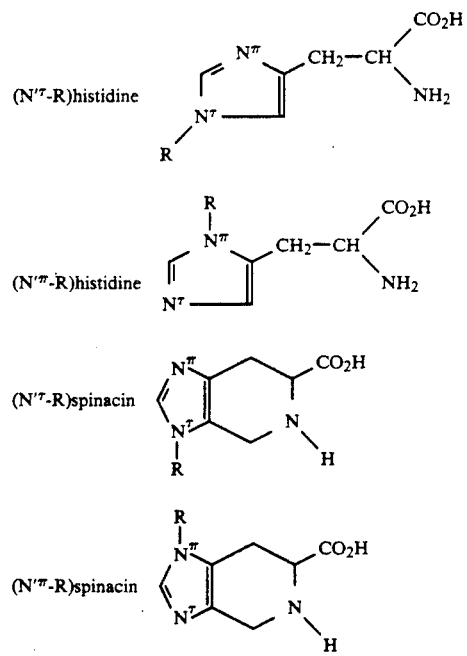

The preparation indicated below does not make it possible to obtain the compounds of the invention. On the other hand, it gives a starting product which is useful in the synthesis of products of the invention.

PREPARATION A :
(Imidazo[1,2-a]pyridin-2-yl)alanine

Stage 1 : 2-Hydroxymethylimidazo[1,2-a]pyridine 200 ml of tetrahydrofuran, 120 mmols of lithium aluminum hydride and then, over 40 minutes, with stirring, 120 mmols of 2-carbethoxyimidazo[1 2a]pyridine prepared according to the method described by J.G. LOMBARDINO (J. Org. Chem., 30, 2403-2407, 1965) in solution in 150 ml of tetrahydrofuran are introduced into a round bottomed flask under a nitrogen atmosphere. The stirring is maintained for 20 hours at room temperature. The mixture is hydrolyzed with 50 ml of isopropanol and then with 50 ml of a saturated solution of sodium chloride. After evaporating to dryness, the expected product is obtained after purification on a silica column (elution solvent: dichloromethane/methanol: 95/5).
Yield: 31%

Stage 2 : 2-Chloromethylimidazo[1,2-a]pyridine hydrochloride 40 ml of thionyl chloride and then, in fractions, 34 mmols of the product obtained in the preceding stage are introduced into a round bottomed flask. The whole is refluxed for 20 minutes and then evaporated to dryness. The residue is taken up with 100 ml of toluene and evaporated, and then again taken up with 50 ml of isopropanol. The precipitate is then filtered and then washed with dichloromethane.
Yield: 61%

Stage 3 (Imidazo[1,2-a]pyridin-2-yl)alanine 100 ml of ethanol and then, in fractions, 0.056 g-atom of sodium are introduced into a round bottomed flask. When the sodium has reacted, 8.05 g of ethyl acetamidomalonate are added and the whole is stirred while allowing the temperature to return to 20° C. 19 mmols of the product obtained in the preceding stage are then added in fractions over 10 minutes. The stirring is maintained for 18 hours at room temperature. After evaporating the ethanol, 200 ml of N-hydrochloric acid are added. This aqueous phase is washed with ethyl acetate and then alkalinized with sodium carbonate and extracted with ethyl acetate. The organic phase is then washed with water and then evaporated. The expected product, which is obtained in the form of a base, is hydrolyzed in hydrochloride form by refluxing for 6 hours in 6N hydrochloric acid, evaporating to dryness, taking up with water and fixing to a resin. It is eluted with 10% ammonium hydroxide which is then evaporated.
Yield: 74%

EXAMPLE 1 :
N-Myristoyl-3-(S)-carboxy-(1,2,3,4)-tetrahydroisoquinoline

Stage 1 : N-Hydroxysuceinimide myristate 60 mmols of N-hydroxysuccinimide are dissolved with stirring in 200 ml of ethyl acetate. A solution of 60 mmols of myristic acid in 100 ml ethyl acetate and then 60 mmois of cyclohexylcarbodiimine are then added. After stirring for 20 hours at room temperature, the dicyclohexylurea formed is filtered and the filtrate evaporated. The expected product is obtained after recrystallization in ethanol.
Yield: 75%

Melting point: 83° C.

Stage 2 : N-Myristoyl-3-(S)-carboxy-(1,2,3,4)-tetrahydroisoquinoline

Using the method described by Y. LAPIDOT and S. RAPPOPORT (J. of Lipid. Research, 8, 142-145, 1967), the expected product, which is purified by chromatography on silica gel (elution solvent: $CH_2Cl_2$/MeOH: 95/5), is obtained from the product described in the preceding stage and from 3-(S)-carboxy-(1,2,3,4)-tetrahydroisoquinoline.
Yield: 50%

| Infrared (nujol): | $v_{OH}$ between 3,000 and 2,300 cm$^{-1}$<br>$v_{CO}$ acid: 1,720 cm$^{-1}$<br>$v_{CO}$ amide: 1,640 cm$^{-1}$ | | |
|---|---|---|---|
| Elemental microanalysis: | C % | H % | N % |
| calculated | 74.38 | 9.62 | 3.61 |
| found | 74.47 | 9.72 | 3.61 |

Examples 2 to 14, 17, 18, 20, 22, 28 to 34 and 56 to 59 were synthesized from the raw materials described in the literature according to the same procedure as that described in Example 1.

EXAMPLE 2 :
N-MYRISTOYL-3-(S)-CARBOXY-2-AZABICYCLO[2.2.2] OCTANE
Yield: 16%

| Infrared (nujol): | $v_{OH}$ between 3,700 and 2,000 cm$^{-1}$<br>$v_{CO}$ acid: 1,740 cm$^{-1}$<br>$v_{CO}$ amide: 1,650 cm$^{-1}$ |

EXAMPLE 3 :
N-MYRISTOYL-2-CARBOXY-(2S,3aS,7aS)-PERHYDROINDOLE
Yield: 44%

| Infrared (nujol): | $v_{OH}$ between 3,700 and 2,250 cm$^{-1}$<br>$v_{CO}$ acid: 1,740 cm$^{-1}$<br>$v_{CO}$ amide I: 1,640 cm$^{-1}$<br>$v_{CO}$ amide II: 1,600 cm$^{-1}$ |

EXAMPLE 4 :
N-MYRISTOYL-1-CARBOXYISOINDOLINE
Yield: 54%

| Infrared (nujol): | $v_{OH}$ between 3,500 and 2,200 cm$^{-1}$<br>$v_{CO}$ acid: 1,743 cm$^{-1}$<br>$v_{CO}$ amide: 1,603 cm$^{-1}$ | | |
|---|---|---|---|
| Elemental microanalysis: | C % | H % | N % |
| calculated | 73.96 | 9.44 | 3.75 |
| found | 73.60 | 9.43 | 3.76 |

EXAMPLE 5 :
N-MYRISTOYL-(N't-BENZYL)-(S)-HISTIDINE
Yield: 28%

| Infrared (nujol): | $v_{NH}$: 3,300 cm$^{-1}$<br>$v_{OH}$ between 3,200 and 1,800 cm$^{-1}$<br>$v_{CO}$ acid: 1,700 cm$^{-1}$ |

| | | | |
|---|---|---|---|
| | $v_{CO}$ amide: 1,640 cm$^{-1}$ | | |
| Elemental microanalysis: | C % | H % | N % |
| calculated | 71.17 | 9.07 | 9.22 |
| found | 70.74 | 9.35 | 9.25 |

EXAMPLE 6 :
N-MYRISTOYL-(N't-TOSYL)-(S)-histidine

Yield: 55%

| | |
|---|---|
| Infrared (nujol): | $v_{NH}$ between 3,600 and 2,400 cm$^{-1}$ |
| | $v_{CO}$ carboxylate and amide 1,640 cm$^{-1}$ |

EXAMPLE 7 :
N-MYRISTOYL-(N't-TRITYL)-(S)-HISTIDINE

Yield: 65%

| | |
|---|---|
| Infrared (nujol): | $v_{OH}$ and $V_{NH}$ around 3,300 cm$^{-1}$ |
| | $v_{CO}$ amide: 1,651 cm$^{-1}$ |

EXAMPLE 8 :
MYRISTOYL-(N'N-BENZYLOXYMETHYL)-(S)-HISTIDINE

Yield: 49%

| | |
|---|---|
| Infrared (nujol): | $v_{NH}$ 3,317 cm$^{-1}$ |
| | $v_{OH}$ between 2,500 and 2,000 cm$^{-1}$ |
| | $v_{CO}$ acid: 1,714 cm$^{-1}$ |
| | $v_{CO}$ amide: 1,645 cm$^{-1}$ |

Melting point: 128° C

| Elemental microanalysis: | C % | H % | N % |
|---|---|---|---|
| calculated | 69.25 | 8.92 | 8.65 |
| found | 68.72 | 8.88 | 8.53 |

EXAMPLE 9 :
N-MYRISTOYL-(4-HYDROXY-3,5-DITERBUTYL-PHENYL)ALANINE

Yield: 36%

| | |
|---|---|
| Infrared (nujol): | $v_{OH}$ phenol: 3,630 cm$^{-1}$ |
| | $v_{OH}$ between 3,600 and 2,300 cm$^{-1}$ |
| | $v_{CO}$ acid: 1,730 cm$^{-1}$ |

EXAMPLE 10 :
N-MYRISTOYL-α-ETHYLPHENYLGLYCINE

Yield: 31%
Melting point : 128° C

| | |
|---|---|
| Infrared (nujol): | $v_{NH}$ 3,400 cm$^{-1}$ |
| | $v_{OH}$ between 3,200 and 1,800 cm$^{-1}$ |
| | $v_{CO}$ acid: 1,690 cm$^{-1}$ |
| | $v_{CO}$ amide I: 1,620 cm$^{-1}$ |
| | $v_{CO}$ amide II: 1,520 cm$^{-1}$ |

| Elemental microanalysis | C % | H % | N % |
|---|---|---|---|
| calculated | 73.99 | 10.09 | 3.60 |
| found | 73.54 | 10.26 | 3.62 |

EXAMPLE 11 :
N-MYRISTOYL-P-(DIETHYLPHOSPHONOMETHYL)PHENYLALANINE

The p-(diethylphosphonomethyl)phenylalanine used is described by I. MARSEIGNE and B.P. ROQUES (J. Org. Chem., 53, 3621–3624, 1988).

Yield: 11%

| | |
|---|---|
| Infrared (nujol): | $v_{NH}$ 3,600 cm$^{-1}$ |
| | $v_{OH}$ between 3,500 and 2,000 cm$^{-1}$ |
| | $v_{CO}$ acid: 1,720 cm$^{-1}$ |
| | $v_{CO}$ amide I: 1,640 cm$^{-1}$ |
| | $v_{CO}$ amide II: 1,520 cm$^{-1}$ |

| Elemental microanalysis | C % | H % | N % |
|---|---|---|---|
| calculated | 63.98 | 9.20 | 2.66 |
| found | 63.94 | 9.20 | 2.49 |

EXAMPLE 12 :
N-MYRISTOYL-α-METHYLPHENYLALANINE

Yield : 62%

| | |
|---|---|
| Infrared: | $v_{NH}$ 3,290 cm$^{-1}$ |
| | $v_{OH}$ between 3,300 and 2,300 cm$^{-1}$ |
| | $v_{CO}$ acid: 1,720 cm$^{-1}$ |
| | $v_{CO}$ amide: 1,620 cm$^{-1}$ |

| Elemental microanalysis: | C % | H % | N % |
|---|---|---|---|
| calculated | 73.99 | 10.09 | 3.60 |
| found | 73.87 | 10.18 | 3.42 |

EXAMPLE 13 : N-MYRISTOYLSPINACIN

Yield: 22%

| | |
|---|---|
| Infrared (nujol): | $v_{OH}$ between 3,700 and 2,300 cm$^{-1}$ |
| | $v_{CO}$ amide: 1,614 cm$^{-1}$ |

EXAMPLE 14 : DIETHYL 1-MYRISTOYLAMINO-2-PHENYLETHANE-PHOSPHONATE

Yield: 51%

| | |
|---|---|
| Infrared (liquid film): | $v_{NH}$ 3,260 cm$^{-1}$ |
| | $v_{CO}$ amide I ≈ 1,670 cm$^{-1}$ |
| | $v_{CO}$ amide II: 1,540 cm$^{-1}$ |

| Elemental microanalysis: | C % | H % | N % |
|---|---|---|---|
| calculated | 64.21 | 9.31 | 3.40 |
| found | 63.99 | 9.12 | 3.36 |

EXAMPLE 15 :
1-MYRISTOYLAMINO-2-PHENYLETHANE-PHOSPHONIC ACID

The expected product is obtained by total saponification of 37 mmols of the compound described in Example 14 in the presence of 7.5 ml of acetic acid and 1.85 ml of 48% hydrobromic acid, by evaporation and recrystallization in an acetone/water (3/1) mixture.

Yield: 76%

Melting point: 108° C.

| Infrared (nujol): | $v_{NH}$: 3,600 cm$^{-1}$ | | |
|---|---|---|---|
| | $v_{OH}$ between 3,400 and 2,000 cm$^{-1}$ | | |
| Elemental microanalysis: | C % | H % | N % |
| calculated | 64.21 | 9.31 | 3.40 |
| found | 63.99 | 9.84 | 3.36 |

EXAMPLE 16 : ETHYL 1-MYRISTOYLAMINO-2-PHENYLETHANEHYDROGENOPHOSPHONATE

The expected product is obtained by partial saponification of 11 mmols of the compound described in Example 14 in the presence of 10 ml of ethanol and 1.1 ml of 1N potassium hydroxide, and after refluxing for 72 hours. The ethanol is evaporated and 50 ml of water are added. The aqueous phase is washed with pentane, acidified to pH=1 with concentrated hydrochloric acid. The product is then extracted with ethyl acetate and purified by chromatography on a silica column (eluent: dichloromethane/methanol: 80/20).
Yield: 21%

| Infrared (nujol): | $v_{NH}$: 3,380 cm$^{-1}$ |
|---|---|
| | $v_{CO}$ amide: 1,580 cm$^{-1}$ |

EXAMPLE 17 : 1-MYRISTOYLAMINO-2-PHENYLETHANEPHOSPHINIC ACID

The 1-amino-2-phenylethanephosphinic acid used is described in J. Chem. Soc., Perkin Trans., 1, 2845–2853, 1984. Purificaton by recrystallization in ethyl acetate.
Yield: 81%
Melting point: 108° C.

| Infrared (nujol): | $v_{NH}$: 3,290 cm$^{-1}$ | | |
|---|---|---|---|
| | $v_{OH}$ between 3,100 and 2,000 cm$^{-1}$ | | |
| | $v_{CO}$ amide ≈ 1,650 cm$^{-1}$ | | |
| Elemental microanalysis: | C % | H % | N % |
| calculated | 66.81 | 9.68 | 3.64 |
| found | 66.76 | 9.57 | 3.54 |

EXAMPLE 18 : DIETHYL MYRISTOYLAMINOMETHANEPHOSPHONATE

Yield : 60%

| Infrared: | $v_{NH}$: 3,280 cm$^{-1}$ |
|---|---|
| | $v_{CO}$ amide I: 1,650 cm$^{-1}$ |
| | $v_{CO}$ amide II: 1,550 cm$^{-1}$ |

EXAMPLE 19 : MYRISTOYLAMINOMETHANEPHOSPHONIC ACID

By carrying out the procedure as in Example 15 but saponifying the compound described in Example 18, the expected product is obtained.
Yield : 58%

| Infrared (nujol): | $v_{NH}$: 3,260 cm$^{-1}$ |
|---|---|

| | $v_{OH}$ between 3,500 and 2,000 cm$^{-1}$ | | |
|---|---|---|---|
| | $v_{CO}$ amide I: 1,650 cm$^{-1}$ | | |
| | $v_{CO}$ amide II: 1,550 cm$^{-1}$ | | |
| Elemental microanalysis: | C % | H % | N % |
| calculated | 56.06 | 10.03 | 4.35 |
| found | 56.38 | 10.36 | 4.33 |

EXAMPLE 20 : DIETHYL 1-(S)-MYRISTOYLAMINOETHANEPHOSPHONATE

Yield: 55%

EXAMPLE 21 : 1-(S)-MYRISTOYLAMINOETHANEPHOSPHONIC ACID

By carrying out the procedure as in Example 15 but saponifying the compound described in Example 20, the expected product is obtained.
Yield : 49%

| Infrared (nujol): | $v_{NH}$: 3,280 cm$^{-1}$ | | |
|---|---|---|---|
| | $v_{OH}$ between 3,600 and 2,000 cm$^{-1}$ | | |
| | $v_{CO}$ amide I: 1,650 cm$^{-1}$ | | |
| | $v_{CO}$ amide II: 1,540 cm$^{-1}$ | | |
| Elemental microanalysis: | C % | H % | N % |
| calculated | 57.29 | 10.22 | 4.17 |
| found | 57.50 | 10.13 | 4.08 |

EXAMPLE 22 : DIETHYL 1-(R)-MYRISTOYLAMINOETHANEPHOSPHONATE

Yield: 52%

EXAMPLE 23 : 1-(R)-MYRISTOYLAMINOETHANEPHOSPHONIC ACID

By carring out the procedure as in Example 15 but saponifying the compound described in Example 22, the expected product is obtained.
Yield : 41%

| Infrared (nujol): | $v_{NH}$: 3,280 cm$^{-1}$ | | |
|---|---|---|---|
| | $v_{OH}$ between 3,500 and 2,000 cm$^{-1}$ | | |
| | $v_{CO}$ amide I: 1,650 cm$^{-1}$ | | |
| | $v_{CO}$ amide II: 1,540 cm$^{-1}$ | | |
| Elemental microanalysis: | C % | H % | N % |
| calculated | 57.29 | 10.22 | 4.17 |
| found | 57.21 | 10.10 | 4.02 |

EXAMPLE 24: N-MYRISTOYL-(S)-β-CYCLOHEXYLALANINE (S)-β- Cyclohexylalanine is prepared according to the process described in J. Med. Chem., 15 (8), 794, 1972.
Yield : 60%
Melting point : 88° C.

| Infrared (nujol): | $v_{NH}$: 3,340 cm$^{-1}$ |
|---|---|
| | $v_{OH}$ between 3,300 and 2,000 cm$^{-1}$ |
| | $v_{CO}$ acid: 1,720 cm$^{-1}$ |

-continued

| | | |
|---|---|---|
| | $\nu_{CO}$ amide I: 1,620 cm$^{-1}$ | |
| | $\nu_{CO}$ amide II: 1,560 cm$^{-1}$ | |

| Elemental microanalysis: | C % | H % | N % |
|---|---|---|---|
| calculated | 72.39 | 11.36 | 3.67 |
| found | 72.40 | 11.30 | 3.59 |

EXAMPLE 25 : CARBOXAMIDOMETHYL N-MYRISTOYL-(S)-PHENYLALANINATE 4 mmols of N-myristoyl-(S)-phenylalanine are solubilized in 15 ml of methanol and 1.5 ml of water. 4.6 ml of a 20% aqueous solution of cesium carbonate are added to this mixture and the whole is stirred for 10 minutes. After evaporating the solvents and drying, the residue is dissolved in 20 ml of dimethylformamide. 44 mmols of chloroacetamide are then added and the whole is stirred for 20 hours at room temperature. After evaporating the solvent, the residue is taken up with water and extracted with ethyl acetate. The expected product is then obtained after evaporation and recrystallization in isopropyl oxide.

Yield : 18%
Melting point : 104° C

| Infrared (nujol): | $\nu_{NH}$ 3,354, 3,307 and 3,159 cm$^{-1}$ | | |
|---|---|---|---|
| | $\nu_{CO}$ ester: 1,757 cm$^{-1}$ | | |
| | $\nu_{CO}$ amide I: 1,739 and 1,707 cm$^{-1}$ | | |
| | $\nu_{CO}$ amide II: 1,635 and 1,620 cm$^{-1}$ | | |

| Elemental microanalysis: | C % | H % | N % |
|---|---|---|---|
| calculated | 69.41 | 9.32 | 6.47 |
| found | 69.11 | 9.48 | 6.33 |

EXAMPLE 26 : GLYCEROLACETONIDE N-MYRISTOYL-(S)-PHENYLALANINATE 5 mmols of N-myristoylphenylalanine are dissolved in 50 ml of dichloromethane and then 5 mmols of triethylamine are added to this solution while cooling to 0° C. A solution containing 55 mmols of isobutylchloroformate in 10 ml of dichloromethane is slowly added to the preceding mixture, and then 5 mmols of 4-dimethylaminopyridine, while maintaining the whole at 0° C. Finally, after adding a solution containing 5 mmols of glycerol isopropylidene in 10 ml of dichloromethane, the whole is stirred for 18 hours at room temperature. The dichloromethane is evaporated and the residue taken up with 50 ml of ethyl acetate. The solution is washed with a saturated solution of sodium bicarbonate and then with water. After drying and evaporation, the expected product is obtained after purification on a silica column (elution solvent: dichloromethane/ethyl acetate: 90/10).

Yield : 52%

| Infrared (nujol): | $\nu_{NH}$ 3,300 cm$^{-1}$ | | |
|---|---|---|---|
| | $\nu_{CO}$ ester: 1,740 cm$^{-1}$ | | |
| | $\nu_{CO}$ amide I: 1,640 cm$^{-1}$ | | |
| | $\nu_{CO}$ amide II: 1,540 cm$^{-1}$ | | |

| Elemental microanalysis: | C % | H % | N % |
|---|---|---|---|
| calculated | 71.13 | 9.67 | 2.86 |
| found | 71.07 | 9.87 | 2.77 |

EXAMPLE 27 : GLYCEROL N-MYRISTOYL-(S)-PHENYLALANINATE 15 mmols of the product obtained in Example 26 are dissolved in 5 ml of methanol and 1.5 ml of N hydrochloric acid. The solution is allowed to stand for 48 hours at room temperature. After evaporation, the expected product is obtained after purification on a silica column (elution solvent: dichloromethane/methanol: 97/3).

Yield : 51%

| Infrared (nujol): | $\nu_{NH}$ and $\nu_{OH}$ between 3,600 and 3,100 cm$^{-1}$ | | |
|---|---|---|---|
| | $\nu_{CO}$ ester: 1,736 cm$^{-1}$ | | |
| | $\nu_{CO}$ amide: 1,647 cm$^{-1}$ | | |

| Elemental microanalysis: | C % | H % | N % |
|---|---|---|---|
| calculated | 69.45 | 9.64 | 3.11 |
| found | 69.41 | 9.74 | 3.01 |

EXAMPLE 28 : N-MYRISTOYL-(IMIDAZO[1,2-A]PYRIDIN-2-YL)ALANINE

The (imidazo[1,2-a]pyridin-2-yl)alanine used is described in preparation A.

Yield : 25%

| Infrared (nujol): | $\nu_{NH}$ 3,288 cm$^{-1}$ |
|---|---|
| | $\nu_{CO}$ carboxylate and amide: 1,635 cm$^{-1}$ |
| | $\nu_{C=C}$ 1,591 cm$^{-1}$ |

EXAMPLE 29 : N-MYRISTOYL-(N'T-BENZYL)SPINACIN

Yield : 23%

| Infrared (nujol): | $\nu_{OH}$ between 3,600 and 2,000 cm$^{-1}$ |
|---|---|
| | $\nu_{CO}$ : 1,639 cm$^{-1}$ |
| | $\nu_{CO}$ carboxylate: 1,600 cm$^{-1}$ |

EXAMPLE 30 : N-MYRISTOYL-(N'N-BENZYL)SPINACIN

Yield : 25%

| Infrared (nujol): | $\nu_{OH}$ between 3,600 and 2,000 cm$^{-1}$ |
|---|---|
| | $\nu_{CO}$ acid: 1,720 cm$^{-1}$ |
| | $\nu_{CO}$ amide: 1,641 cm$^{-1}$ |

EXAMPLE 31 : N-PALMITOYL-(N'T-BENZYL0HISTIDINE

Yield : 50%

| Infrared (nujol): | $\nu_{NH}$ 3,300 cm$^{-1}$ | | |
|---|---|---|---|
| | $\nu_{OH}$ between 3,400 and 2,300 cm$^{-1}$ | | |
| | $\nu_{CO}$ amide I: 1,640 cm$^{-1}$ | | |
| | $\nu_{CO}$ amide II: 1,550 cm$^{-1}$ | | |

| Elemental microanalysis: | C % | H % | N % |
|---|---|---|---|
| calculated | 72.01 | 9.38 | 8.69 |
| found | 72.14 | 9.33 | 8.62 |

EXAMPLE 32:
N-LAUROYL-(N'T-BENZYL0HISTIDINE
Yield: 48%

| Infrared (nujol): | $v_{NH}$: 3,200 cm$^{-1}$ |  |  |
|---|---|---|---|
|  | $v_{OH}$ between 3,400 and 2,000 cm$^{-1}$ |  |  |
|  | $v_{CO}$ acid: 1,710 cm$^{-1}$ |  |  |
|  | $v_{CO}$ amide I: 1,640 cm$^{-1}$ |  |  |
|  | $v_{CO}$ amide II: 1,550 cm$^{-1}$ |  |  |
| Elemental microanalysis: | C % | H % | N % |
| calculated | 70.33 | 8.72 | 9.83 |
| found | 69.22 | 8.81 | 9.63 |

EXAMPLE 33:
N-PALMITOYL-P-(DIETHYLPHOSPHONOME-THYL)PHENYLALANINE
Yield: 76%
Melting point: 73° C.

| Infrared (nujol): | $v_{NH}$: 3,280 cm$^{-1}$ |
|---|---|
|  | $v_{OH}$ between 2,800 and 2,500 cm$^{-1}$ |
|  | $v_{CO}$ acid: 1,745 cm$^{-1}$ |
|  | $v_{CO}$ amide I: 1,650 cm$^{-1}$ |
|  | $v_{CO}$ amide II: 1,540 cm$^{-1}$ |

EXAMPLE 34:
N-LAUROYL-P-(DIETHYLPHOSPHONOME-THYL)PHENYLALANINE
Yield: 68%
Melting point: 52° C.

| Infrared (nujol): | $v_{NH}$: 3,270 cm$^{-1}$ |
|---|---|
|  | $v_{OH}$ between 3,000 and 2,400 cm$^{-1}$ |
|  | $v_{CO}$ acid: 1,745 cm$^{-1}$ |
|  | $v_{CO}$ amide I: 1,650 cm$^{-1}$ |
|  | $v_{CO}$ amide II: 1,535 cm$^{-1}$ |

EXAMPLE 35: METHYL N-(TRIDECANEPHOSPHONYL)-(s)-PHENYLALANINATE, MONOSODIUM SALT

Stage 1

2.2 mmols of benzyl tridecanephosphonate chloride obtained according to the method described by K.A. PETNOV (J. GEN. CHEM. USSR, 29, 1465-1467, 1959) are condensed with 2.2 mmols of methyl (S)-phenylalaninate in 10 ml of dichloromethane in the presence of 0.65 ml of triethylamine. The expected product is obtained after evaporating the solvents and purification on a silica column (elution solvent: dichloromethane/ethyl acetate: 9/1).
Yield: 70%

Stage 2: Methyl N-(tridecanephosphonyl)-(S)-phenylalaninate, monosodium salt 1.5 mmols of the product obtained in a preceding stage are hydrogenated in 100 ml of methanol in the presence of 10% palladium on carbon and sodium bicarbonate. After eliminating the catalyst and the solvents, the expected product is obtained after freeze drying.
Yield: 79%

EXAMPLE 36:
N-(12-METHYLTHIOLAUROYL)-(s)-PHENYLALANINE

Stage 1: N-(12-Bromolauroyl)-(S)-phenylalanine

By carrying out the procedure as in Example 1, stage 2, but replacing in stage 2 N-hydroxysuccinimide myristate with N-hydroxysuccinimide 12bromolauroate and 3-(S)-carboxytetrahydro[1,2,3,4]isoquinoline with (S)phenylalanine, the expected product is obtained.
Yield: 61%

Stage 2: N-(12-Methylthiolauroyl)-(S)-phenylalanine 3 mmols of the product obtained in the preceding stage are dissolved in 25 ml of ethanol containing 6 mmols of 85% potassium hydroxide. Bubbling of methylmercaptan is then carried out for 45 minutes and the whole is heated at 60° C. for 5 hours. After cooling and acidifying, the solvents are evaporated. The residue is taken up with 30 ml of ethyl acetate and the solution is washed with water and then with a saturated solution of sodium chloride. The expected product is obtained after evaporating the solvents and purification on a silica column (elution solvent: dichloromethane/ethanol: 97/3).
Yield: 20%

| Infrared (nujol): | $v_{NH}$: 3,303 cm$^{-1}$ |  |  |  |
|---|---|---|---|---|
|  | $v_{OH}$ between 3,500 and 2,400 cm$^{-1}$ |  |  |  |
|  | $v_{CO}$ acid: 1,730 cm$^{-1}$ |  |  |  |
|  | $v_{CO}$ amide: 1,643 cm$^{-1}$ |  |  |  |
| Elemental microanalysis: | C % | H % | N % | S % |
| calculated | 67.14 | 8.96 | 3.56 | 8.15 |
| found | 67.05 | 9.07 | 3.91 | 7.95 |

Examples 37 to 48, 50, 52 to 55 and 60 were prepared according to the same procedure as that described for Example 36, using raw materials described in the literature.

EXAMPLE 37:
N-(11-ETHYLTHIOUNDECANOYL)-(s)-PHENYLALANINE
Yield: 20%
Melting point: 57° C.

| Infrared (nujol): | $v_{NH}$: 3,300 cm$^{-1}$ |  |  |  |
|---|---|---|---|---|
|  | $v_{OH}$ between 3,400 and 2,000 cm$^{-1}$ |  |  |  |
|  | $v_{CO}$ acid: 1,700 cm$^{-1}$ |  |  |  |
|  | $v_{CO}$ amide I: 1,600 cm$^{-1}$ |  |  |  |
|  | $v_{CO}$ amide II: 1,550 cm$^{-1}$ |  |  |  |
| Elemental microanalysis: | C % | H % | N % | S % |
| calculated | 67.13 | 8.96 | 3.56 | 8.14 |
| found | 67.40 | 9.09 | 3.45 | 7.92 |

EXAMPLE 38:
N-(11ETHYLTHIOUNDECANOYL)-(s)-LEUCINE
Yield: 25%

| Infrared (nujol): | $v_{NH}$: 3,327 cm$^{-1}$ |  |  |  |
|---|---|---|---|---|
|  | $v_{OH}$ between 3,000 and 2,500 cm$^{-1}$ |  |  |  |
|  | $v_{CO}$ acid: 1,697 cm$^{-1}$ |  |  |  |
|  | $v_{CO}$ amide I: 1,622 cm$^{-1}$ |  |  |  |
|  | $v_{CO}$ amide II: 1,522 cm$^{-1}$ |  |  |  |
| Elemental microanalysis: | C % | H % | N % | S % |

-continued

| | calculated | 63.47 | 10.37 | 3.90 | 8.92 |
| --- | --- | --- | --- | --- | --- |
| | found | 63.81 | 10.48 | 3.85 | 8.56 |

EXAMPLE 39 : DIETHYL 1-(11-ETHYLTHIOUNDECANOYLAMINO)-2-PHENYLETHANEPHOSPHONATE

Yield : 23%

| Infrared (liquid film): | $v_{NH}$: 3,267 cm$^{-1}$ | | | |
| --- | --- | --- | --- | --- |
| | $v_{CO}$: 1,660 cm$^{-1}$ | | | |
| Elemental microanalysis: | C % | H % | N % | S % |
| calculated | 61.83 | 9.13 | 2.88 | 6.60 |
| found | 61.84 | 9.33 | 2.96 | 6.66 |

EXAMPLE 40 : CARBOXAMIDOMETHYL N-(11-ETHYLTHIOUNDECANOYL)-(S)-PHENYLALANINATE

Yield : 32%

| Infrared (chloroform): | $v_{NH}$: 3,400 cm$^{-1}$ | | | |
| --- | --- | --- | --- | --- |
| | $v_{CO}$ ester: 1,739 cm$^{-1}$ | | | |
| | $v_{CO}$ amide: 1,637 and 1,620 cm$^{-1}$ | | | |
| Elemental microanalysis: | C % | H % | N % | S % |
| calculated | 63.97 | 8.50 | 6.22 | 7.12 |
| found | 64.03 | 8.68 | 6.18 | 6.73 |

EXAMPLE 41 : N-(11-ETHYLTHIOUNDECANOYL)-(N'T-BENZYL)-(S)-HISTIDINE

Yield : 24%

| Infrared (nujol): | $v_{NH}$: 3,315 cm$^{-1}$ | | | |
| --- | --- | --- | --- | --- |
| | $v_{CO}$ acid: 1,705 cm$^{-1}$ | | | |
| | $v_{CO}$ amide: 1,643 cm$^{-1}$ | | | |
| Elemental microanalysis: | C % | H % | N % | S % |
| calculated | 65.93 | 8.30 | 8.87 | 6.77 |
| found | 66.00 | 8.57 | 8.58 | 6.17 |

EXAMPLE 42 : N-(11-ETHYLTHIOUNDECANOYL)-α-ETHYL-α-PHENYLGLYCINE

Yield : 35%

| Infrared (nujol): | $v_{NH}$ and $v_{OH}$ between 3,700 and 2,000 cm$^{-1}$ | | | |
| --- | --- | --- | --- | --- |
| | $v_{CO}$ acid: 1,743 cm$^{-1}$ | | | |
| | $v_{CO}$ amide: 1,637 cm$^{-1}$ | | | |
| Elemental microanalysis: | C % | H % | N % | S % |
| calculated | 67.77 | 9.15 | 3.44 | 7.87 |
| found | 67.61 | 9.29 | 3.55 | 7.70 |

EXAMPLE 43 : N-(11-ETHYLTHIOUNDECANOYL)-4-HYDROXY-3,5-DITERBUTYLPHENYLALANINE

Yield : 19%

| Infrared: | $v_{OH}$: 3,643 cm$^{-1}$ |
| --- | --- |
| | $v_{CO}$ amide I: 1,650 cm$^{-1}$ |
| | $v_{CO}$ amide II: 1,568 cm$^{-1}$ |

EXAMPLE 44 : N-(11-ETHYLTHIOUNDECANOLY)-(S)-β-CYCLOHEXYLALANINE

Yield : 32%

| Infrared (nujol): | $v_{NH}$: 3,332 cm$^{-1}$ | | | |
| --- | --- | --- | --- | --- |
| | $v_{OH}$ between 3,600 and 1,800 cm$^{-1}$ | | | |
| | $v_{CO}$ acid: 1,697 cm$^{-1}$ | | | |
| | $v_{CO}$ amide: 1,622 cm$^{-1}$ | | | |
| Elemental microanalysis: | C % | H % | N % | S % |
| calculated | 66.12 | 10.34 | 3.50 | 8.02 |
| found | 65.67 | 10.40 | 3.66 | 8.23 |

EXAMPLE 45 : N-(11-ETHYLTHIOUNDECANOYL)-(S)-PROLINE

Yield : 40%

| Infrared (liquid film): | $v_{OH}$: 2,800 cm$^{-1}$ | | | |
| --- | --- | --- | --- | --- |
| | $v_{CO}$ acid: 1,743 cm$^{-1}$ | | | |
| | $v_{CO}$ amide: 1,651 cm$^{-1}$ | | | |
| Elemental microanalysis: | C % | H % | N % | S % |
| calculated | 62.93 | 9.68 | 4.08 | 9.33 |
| found | 62.80 | 9.32 | 4.23 | 9.24 |

EXAMPLE 46 : N-(11-ETHYLTHIOUNDECANOYL)-3-(S)-CARBOXY-(1,2,3,4)-TETRAHYDROISOQUINOLINE

Yield : 32%

| Infrared (chloroform): | $v_{OH}$ between 3,600 and 2,000 cm$^{-1}$ |
| --- | --- |
| | $v_{CO}$ acid: 1,720 cm$^{-1}$ |
| | $v_{CO}$ amide: 1,610 cm$^{-1}$ |

EXAMPLE 47 : N-(5-OCTYLTHIOPENTANOYL)-(S)-PHENYLALANINE

Yield : 40%

| Infrared (nujol): | $v_{NH}$: 3,302 cm$^{-1}$ | | | |
| --- | --- | --- | --- | --- |
| | $v_{OH}$ between 3,400 and 1,850 cm$^{-1}$ | | | |
| | $v_{CO}$ acid: 1,709 cm$^{-1}$ | | | |
| | $v_{CO}$ amide: 1,616 cm$^{-1}$ | | | |
| Elemental microanalysis: | C % | H % | N % | S % |
| calculated | 67.14 | 8.96 | 3.56 | 8.15 |
| found | 66.20 | 8.87 | 3.30 | 7.60 |

EXAMPLE 48 : Ethyl N-(12-METHOXYLAUROYL)-(S)-PHENYLALANINATE

The expected product is obtained according to the same procedure as that described in Example 36 but in stage 2, methylmercaptan is replaced with 2 equivalents of sodium methylate.

Yield : 50%

| Infrared (nujol): | $v_{NH}$: 3,300 cm$^{-1}$ |  |  |
|---|---|---|---|
|  | $v_{CO}$ ester: 1,732 cm$^{-1}$ |  |  |
|  | $v_{CO}$ amide: 1,645 cm$^{-1}$ |  |  |
| Elemental microanalysis: | C % | H % | N % |
| calculated | 71.07 | 9.69 | 3.45 |
| found | 71.30 | 9.75 | 3.44 |

EXAMPLE 49 :
N-(12-METHOXYLAUROYL)-(S)-PHENYLALA-NINE

The expected product is obtained by saponification, in N potassium hydroxide in methanolic medium, of the compound described in Example 48.
Yield : 88%

| Infrared (nujol): | $v_{NH}$: 3,352 cm$^{-1}$ |  |  |
|---|---|---|---|
|  | $v_{OH}$ between 3,500 and 2,200 cm$^{-1}$ |  |  |
|  | $v_{CO}$ acid: 1,701 cm$^{-1}$ |  |  |
|  | $v_{CO}$ amide I: 1,676 cm$^{-1}$ |  |  |
|  | $v_{CO}$ amide II: 1,525 cm$^{-1}$ |  |  |
| Elemental microanalysis: | C % | H % | N % |
| calculated | 69.99 | 9.34 | 3.71 |
| found | 69.31 | 9.69 | 3.48 |

EXAMPLE 50 : DIETHYL 1-(12-METHOXYLAUROYLAMINO)-2-PHENYLETHANEPHOSPHONATE

The expected product is obtained according to the same procedure as that described in Example 48.
Yield : 25%

| Infrared (nujol): | $v_{NH}$: 3,269 cm$^{-1}$ |  |  |
|---|---|---|---|
|  | $v_{CO}$ amide I: 1,678 cm$^{-1}$ |  |  |
|  | $v_{CO}$ amide II: 1,541 cm$^{-1}$ |  |  |
| Elemental microanalysis: | C % | H % | N % |
| calculated | 63.94 | 9.44 | 2.98 |
| found | 63.83 | 9.51 | 2.86 |

EXAMPLE 51:1-(12-METHOXYLAUROYLAMINO)-2-PHENYLETHANEPHOSPHONIC ACID

The expected product is obtained by saponification of the compound described in Example 50 in potassium hydroxide in ethanolic medium in the presence of tetrabutylammonium bromide, for 2 hours at 60° C.
Yield : 20%

| Infrared (nujol) | $v_{NH}$: 3,282 cm$^{-1}$ |
|---|---|
|  | $v_{CO}$ amide: 1,645 cm$^{-1}$ |

EXAMPLE 52 :
N-(10-PROPYLOXYDECANOYL)-(S)-PHENYLALANINE

The expected product is obtained according to the same procedure as that described in Example 36 but in stage 2, methylmercaptan is replaced with 2 equivalents of sodium propanolate.
Yield : 15%

| Infrared liquid film: | $v_{NH}$ and $v_{OH}$ between 3,600 and 1,900 cm$^{-1}$ |  |  |
|---|---|---|---|
|  | $v_{CO}$ acid: 1,738 cm$^{-1}$ |  |  |
|  | $v_{CO}$ amide I: 1,649 cm$^{-1}$ |  |  |
|  | $v_{CO}$ amide II: 1,543 cm$^{-1}$ |  |  |
| Elemental microanalysis: | C % | H % | N % |
| calculated | 69.99 | 9.34 | 3.71 |
| found | 69.71 | 9.45 | 3.79 |

EXAMPLE 53 :
N-(10-PROPARGYLOXYDECANOYL)-(S)-PHENYLALANINE

The expected product is obtained according to the same procedure as that described in Example 36 but in stage 2, methylmercaptan is replaced with 2 equivalents of sodium propargylate.
Yield : 25%

| Infrared (nujol): | $v_{NH}$ and $v_{OH}$ between 3,600 and 1,800 cm$^{-1}$ |  |  |
|---|---|---|---|
|  | $v_{CO}$ acid: 1,734 cm$^{-1}$ |  |  |
|  | $v_{CO}$ amide I: 1,649 cm$^{-1}$ |  |  |
|  | $v_{CO}$ amide II: 1,535 cm$^{-1}$ |  |  |
| Elemental microanalysis: | C % | H % | N % |
| calculated | 70.75 | 8.37 | 3.75 |
| found | 70.35 | 8.25 | 3.99 |

EXAMPLE 54 :
N-(P-DECYLBENZOYL)-(S)-PHENYLALANINE

The expected product is obtained according to the same procedure as that described for Example 1 but in stage 1, myristic acid is replaced with p-decylbenzoic acid.
Yield : 90%
Melting Point : 109° C.

| Infrared (nujol): | $v_{NH}$: 3,320 cm$^{-1}$ |  |  |
|---|---|---|---|
|  | $v_{OH}$ between 3,000 and 2,300 cm$^{-1}$ |  |  |
|  | $v_{CO}$ acid: 1,725 cm$^{-1}$ |  |  |
|  | $v_{CO}$ amide: 1,635 cm$^{-1}$ |  |  |
| Elemental microanalysis: | C % | H % | N % |
| calculated | 76.25 | 8.61 | 3.42 |
| found | 75.50 | 8.64 | 3.39 |

EXAMPLE 55 :
N-(P-DECYLBENZOYL)GLYCINE

The procedure is the same as that described in Example 54.
Yield : 59%
Melting point : 134° C.

| Infrared (nujol): | $v_{NH}$: 3,320 cm$^{-1}$ |  |  |
|---|---|---|---|
|  | $v_{OH}$ between 3,100 and 2,300 cm$^{-1}$ |  |  |
|  | $v_{CO}$ acid: 1,740 cm$^{-1}$ |  |  |
|  | $v_{CO}$ amide: 1,620 cm$^{-1}$ |  |  |
| Elemental microanalysis: | C % | H % | N % |
| calculated | 71.44 | 9.15 | 4.38 |
| found | 71.25 | 9.05 | 4.23 |

EXAMPLE 56: N-(12-HYDROXYLAUROYL)-(S)-PHENYLALANINE

The expected product is obtained according to the same procedure as that described for Example 1 but in stage 1, myristic acid is replaced with 12-hydroxylauric acid.

Yield: 85%
Melting point: 90° C.

| Infrared (nujol): | $v_{NH}$ and $v_{OH}$ between 3,583 and 1,800 cm$^{-1}$ |
| --- | --- |
| | $v_{CO}$ acid: 1,720 cm$^{-1}$ |
| | $v_{CO}$ amide I: 1,647 cm$^{-1}$ |
| | $v_{CO}$ amide II: 1,539 cm$^{-1}$ |

| Elemental microanalysis: | C % | H % | N % |
| --- | --- | --- | --- |
| calculated | 69.39 | 9.15 | 3.85 |
| found | 68.73 | 9.18 | 3.51 |

EXAMPLE 57: N-MYRISTOYL-2-(S)-CARBOXYINDOLINE

| Elemental microanalysis: | C % | H % | N % |
| --- | --- | --- | --- |
| calculated | 73.96 | 9.44 | 3.75 |
| found | 74.00 | 9.29 | 3.99 |

EXAMPLE 58: N-MYRISTOYL-3-(S)-CARBOXY-1,2,3,4-TETRAHYDRO-β-CARBOLINE

| Elemental microanalysis: | C % | H % | N % |
| --- | --- | --- | --- |
| calculated | 73.20 | 8.98 | 6.57 |
| found | 72.85 | 9.04 | 6.58 |

EXAMPLE 59: N-MYRISTOYL-2-CARBOXYPIPERIDINE

| Elemental microanalysis | C % | H % | N % |
| --- | --- | --- | --- |
| calculated | 70.75 | 10.98 | 4.13 |
| found | 70.78 | 11.00 | 4.44 |

EXAMPLE 60: N-(10-PROPYLTHIODECANOYL)-(S)-PHENYLALANINE

| Elemental microanalysis: | C % | H % | N % | S % |
| --- | --- | --- | --- | --- |
| calculated | 67.14 | 8.96 | 3.56 | 8.15 |
| found | 67.11 | 8.95 | 3.59 | 7.92 |

EXAMPLE 61: N-(12-METHOXYLAUROYL)GLYCINE

The expected product is obtained according to the same procedure as that described in Example 48.

| Infrared: | $v_{CO}$ acid: 1,703 cm$^{-1}$ |
| --- | --- |
| | $v_{CO}$ amide: 1,645 cm$^{-1}$ |

EXAMPLE 62: N-(9-METHOXYETHOXYNONANOYL)-(S)-PHENYLALANINE

The expected product is obtained according to the same procedure as that described in Example 48.

| Elemental microanalysis: | C % | H % | N % |
| --- | --- | --- | --- |
| calculated | 66.46 | 8.76 | 3.69 |
| found | 65.88 | 8.86 | 3.81 |

PHARMACOLOGICAL STUDY OF THE DERIVATIVES OF THE INVENTION

EXAMPLE 63: INHIBITION OF THE CYTOSOLIC NMT ACTIVITY OF CANCEROUS L1210 CELLS BY THE COMPOUNDS OF THE INVENTION

Mass-cultured L1210 cells (murine leukemia) are used as a source of NMR.

They are cultured in RPMI 1640 supplemented with 50 U/ml of penicillin, 50 μM of streptomycin, 2 mM of glutamine, 10 mM HEPES and 10% of fetal calf serum, maintained in a 5% $CO_2$/95% air atmosphere and at 37° C.

They are harvested and then washed in PBS by centrifuging at low speed. The final cell pellet is resuspended in a 50 mM HEPES buffer, pH 7.4, containing 2 mM EGTA, 1 mM DTT and 1 mM PMSF. The cells are opened by sonication at 4° C. and homogenized by a to and fro movement in a glass/glass Potter. The cell homogenate is then centrifuged at low speed (10,000 rpm, 10 minutes) in order to precipitate the cell debris and the supernatant is subjected to ultracentrifugation at 105,000 g for 1 hour.

The supernatant is then used as a source of NMT. The measurement of activity is carried out according to the method described by Towler and Glazer (PNAS, 1986, 83, 2812) using as substrate peptide either the peptide derived from the NH2 terminal of the pp60src oncogene product: GSSKSKPKDP (DP), or the peptide derived from the NH2 terminal of the gag product, a structural protein of the Maloney murine leucemic virus: GQTVTTPL (T3) at a final concentration of 0.3 mM.

Under these conditions, all the derivatives of the invention exhibit an activity which is substantially higher than that of N-myristoylglycine.

More particularly, the compound from Example 1 exhibits an $IC_{50}$ equal to 1.8 10$^{-7}$ M, that of the compound from Example 5 is equal to 6 10$^{-7}$ m, and finally that of the compound from Example 16 is equal to 2 10$^{-6}$ M.

EXAMPLE 64: INHIBITION OF THE MYRISTOYLATION OF A GAG- DERIVED PEPTIDE OF HIV-1 (SUBTYPE BRU) BY THE COMPOUNDS OF THE INVENTION

Immortalized T lymphocytes (CEM) are mass- cultured as described in Example 57, and then harvested by centrifugation and washed in PBS.

These cells are sonicated (3 brief periods of 10 seconds) and then homogenized in a glass/glass Potter.

This homogenate, in which all the cells have been opened (checked under a microscope), is subjected to centrifugation for 1 h 10) at 105,000 g. The pellet (microsomes) and the supernatant (cytosol) are recovered independently and then frozen.

The NMT activity is then measured following the procedure of Towler and Glaser but stopping the reaction with 200 pl of acetonitrile in order to avoid precipitation of the myristoylated peptide. This 20-AA peptide: NH2$^{GARASVLSGGELDRWEKIRLL}$COOH, is derived from p18 of the HIV-1 virus (subtype BRU).

These experimentations are carried out using a cytosolic (40 μl) or microsomal (20 μl treated with 4 μl of 10% Triton 770) source of CEM cells in the presence of increasing concentrations of the compounds of the invention (1 to 1,000 μM, final). The samples, incubated for 30 minutes at 37° C. and stopped with 200 μl of acetonitrile, are then analyzed by HPLC and the myristoylation of p18 quantified.

Under these conditions, the compound from Example 1 exhibits an IC$_{50}$ equal to $10^{-4}$ M during incubation with the microsomal fraction, and an IC$_{50}$ equal to 8 $10^{-6}$ M during incubation in the cytosol of these CEM cells.

EXAMPLE 65 : PROTECTIVE EFFECT OF THE COMPOUNDS OF THE INVENTION ON CEM CELLS AGAINST INFECTION BY THE HIV VIRUS

The method used is described by WEISLOW et al. (J. Natl. Cancer Inst., 1989, 81, 577).

Under these conditions, the compound from Example 49 shows a protective activity (EC$_{50}$) at a concentration of $10^{-5}$ M and a toxicity (IC$_{50}$) at a concentration of 2 $10^{-4}$ m, the therapeutic index is therefore equal to 20.

EXAMPLE 66 : DIFFERENTIATION OF CULTURED HL60 CELLS BY THE COMPOUNDS OF THE INVENTION

Cultured HL60 cells are treated for 6 days with the compounds dissolved in a minimum of methanol at 9 different concentrations. The doses chosen encompass the IC$_{50}$ determined beforehand using the MTT test (Carmichael et al., Cancer Res., 1986, 47, 936).

The cells are washed (450 μl), resuspended in the same volume of complete medium and incubated for 1 hour at 37° C. in the presence of 7 ug/ml of DNA-specific fluorochrome.

The measurements, which are carried out by means of a laser cytometer, make it possible to estimate the percentage of cells accumulated, and therefore differentiated, in the G0 and G1 phase of the cell cycle.

Under these conditions, the compounds exhibit a marked differentiating effect which can extend to doses below 50 ug/ml, as is the case for the compounds from Examples 1, 16 or 49.

EXAMPLE 67 : PHARMACEUTICAL COMPOSITION

| Tablet: preparation formula for 1,000 tablets containing 2 mg doses of active ingredient. | |
|---|---|
| N-Myristoyl-3-(S)-carboxy-(1,2,3,4)-tetrahydroisoquinoline | 2 g |
| Hydroxypropyl cellulose | 2 g |
| Wheat starch | 10 g |
| Lactose | 100 g |
| Magnesium stearate | 3 g |
| Talc | 3 g |

We claim:

1. A compound selected from those of formula (I)

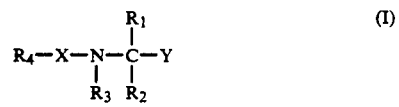

in which:
R$_1$ represents
hydrogen,
linear or branched (C$_1$-C$_6$) alkyl which is unsubstituted or substituted by one or more hydroxyl, amino, carboxyl, carbamoyl, benzylthio, methylthio, mercapto, or unsubstituted phenyl or phenyl substituted by one or more halogen or hydroxyl, linear or branched (C$_1$-C$_6$) alkyl, linear or branched (C$_1$—C$_6$) alkoxy, or (CH$_3$—CH$_2$-O)$_2$PO—CH$_2$—),
phenyl which is unsubstituted or substituted by one or more halogen or hydroxyl or linear or branched (C$_1$-C$_6$) alkyl,
(C$_3$C$_7$) cycloalkyl methyl,
(imidazol-2-yl)methyl or (indol-3- yl)methyl which is unsubstituted or substituted on the heterocycle by benzyl, benzhydryl, trityl, benzyloxymethyl, tosyl, linear or branched (C$_1$—C$_6$) alkyl, or phenyl,
(1-azaindolizin-2yl)methyl of formula and:

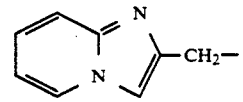

R$_2$ represents hydrogen or linear or branched (C$_1$C$_6$) alkyl,
R$_3$ represents hydrogen or linear or branched (C$_1$-C$_6$) alkyl,
X represents one of the following groups:

Y represents —CO—R5
R$_5$ represents hydroxyl, linear or branched (C$_1$-C$_6$) alkoxy, H$_2$N—CO—CH$_2$-O—, HO—CH$_2$—CHOH—CH$_2$—O—,

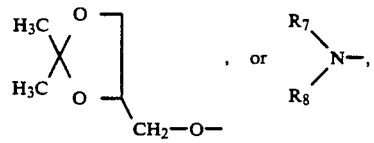

R$_7$ and R$_8$, which are identical or different, represent hydrogen or linear or branched (C$_1$—C$_6$) alkyl, or form with the nitrogen atom to which they are attached, pyrrolidine, piperidine, morpholine, or piperazine,
R$_4$ represents :
1 linear or branched alkyl having 6 to 21 carbon atoms inclusive which are unsubstituted or substituted on the terminal methyl group by hydroxyl, mercapto, phenyl, or ethynyl and in which at least one of the methylene groups is replaced by oxygen or sulfur or by a p-phenylene ring, in the case where:

either

R₁ represents—hydrogen,
—linear or branched ($C_1$-$C_6$) alkyl which is unsubstituted or substituted by one or more hydroxyl, amino, carboxyl, carbamoyl, benzylthio, methylthio, mercapto, or unsubstituted phenyl or phenyl substituted by hydroxyl,
—unsubstituted phenyl,
—(imidazol-2-yl)methyl or (indol-3-yl)methyl which is unsubstituted or substituted on the heterocycle by methyl and

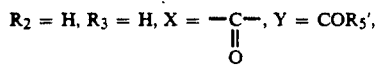

PH(OR₅' being or OH alkoxy, 2 in the other cases :

linear or branched alkyl having 6 to 21 carbon atoms, inclusive which is unsubstituted or substituted on the terminal methyl group by hydroxyl, mercapto, phenyl, or ethynyl and in which one or more methylene groups may be replaced by oxygen or sulfur or by a p-phenylene ring, its isomers, diastereoisomers, and epimers as well as its addition salts with a pharmaceutically acceptable-acid or base.

2. A compound as claimed in claim 1, which is N-(12-methoxylauroyl)phenylalanine, its enantiomers, as well as its addition salts with a pharmaceutically acceptable-base.

3. A method for treating an animal or human living body afflicted with a cancer, the maturation of which involves a myristoylation, comprising the step of administering to the living body a myristoylation-inhibitory amount of a compound of any of claims 1 or 2 which is effective for alleviation of said condition.

4. A pharmaceutical composition useful in the treatment of a cancer or viral disease the maturation of which involves a myristoylation comprising as active principle an effective amount of a compound as claimed in either claims 1 or 2 in combination with one or more pharmaceutically-acceptable excipients or vehicles.

* * * * *

UNITED STATES PATENT AND TRADEMARK OFFICE
CERTIFICATE OF CORRECTION

PATENT NO. : 5,266,576
DATED : Nov. 30, 1993
INVENTOR(S) : Michel Vincent, Georges Remond, Bernard Portevin, Jean-Albert Boutin, Ghanem Atassi It is certified that error appears in the above-indentified patent and that said Letters Patent is hereby corrected as shown below:

Title Page, column 1, [75] Inventors, last line; "Belgium" should read -- France --. (see Issue Notification)
Title Page, column 2, ABSTRACT, line 12; "(C1-C6)" should read --($C_1$-$C_6$)--.
Column 1, line 18; "identif" should read -- identif- --.
Column 3, line 26; "-$CH_2$-o-," should read -- $CH_2$-O-, --.
Column 3, line 53; "($C_1$14 $C_6$)" should read -- ($C_1$-$C_6$) --.
Column 8, approximately line 35; "followina" should read -- following --.
Column 8, lines (approximately) 42-61, in the formulas; "$N^{'T}$" should read -- $N^{'t}$ --, "$N^{'TT}$" should read -- $N^{'II}$ --, "$N^{TT}$" should read -- $N^{II}$ --, and "$N^{T}$" should read -- $N^{t}$ --, in all occurrences - See the formulas as printed below:

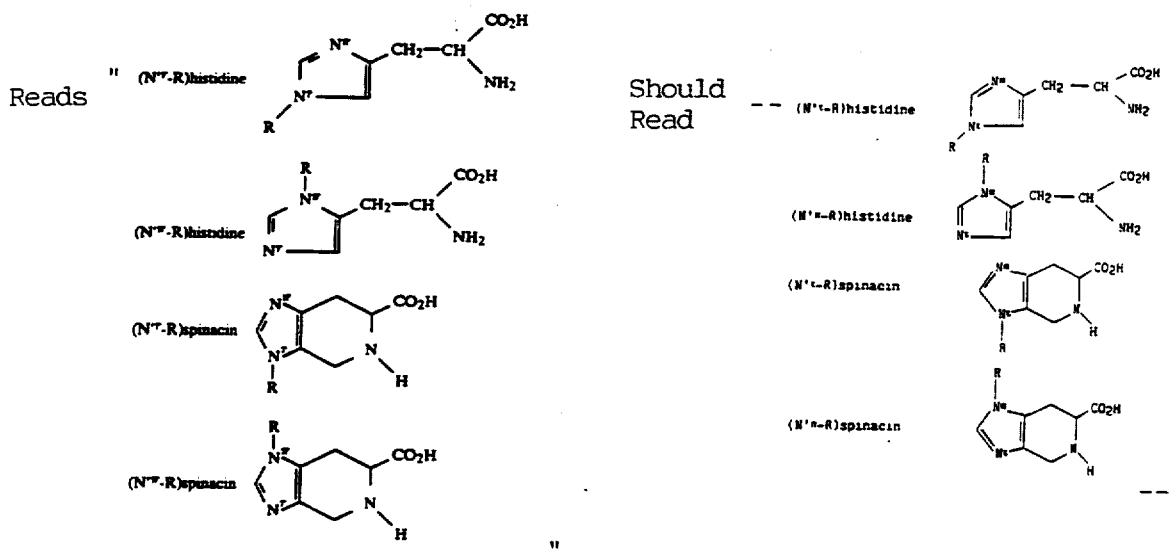

UNITED STATES PATENT AND TRADEMARK OFFICE
CERTIFICATE OF CORRECTION

PATENT NO. : 5,266,576

DATED : November 30, 1993

INVENTOR(S) : Michel Vincent, Georges Remond, Bernard Portevin
Jean-Albert Boutin, Ghanem Atassi It is certified that error appears in the above-indentified patent and that said Letters Patent is hereby corrected as shown below:

Column 9, line 58; "Hydroxysuceinimide" should read -- Hydroxysuccinimide --.
Column 9, line 63; "mmois" should read -- mmols --.
Column 11, approximately line 27; before "MYRISTOYL" insert -- N- --.
Column 11, approximately line 27; "(N'N-" should read -- (N'$^{\tau}$- --.
Column 16, line 37; "N'T" should read -- "N'$^{\tau}$" --.
Column 16, approximately line 47; "(N'N-" should read -- (N'$^{\tau}$- --.
Column 16, line 56; (N'T-BENZYLOHISTIDINE" should read -- (N'$^{\tau}$-BENZYL)HISTIDINE --.
Column 17, line 2; "(N'T-BENZYLOHISTIDINE" should read -- (N'$^{\tau}$-BENZYL)HISTIDINE --.
Column 17, approximately line 44; "-(s)-" should read -- -(S)- --.
Column 18, line 2; "-(s)-" should read -- -(S)- --.
Column 18, line 5; "-Bromolauroly)-" should read -- -Bromolauroyl)- --.
Column 18, line 8; "12bromolauroate" should read -- 12 bromolauroate --.
Column 18, approximately line 43; "-(s)-" should read -- -(S)- --.
Column 18, approximately line 59; "N-(11ETHYLTHIOUNDECANOYL)-(s)-"should read -- N-(11-ETHYLTHIOUNDECANOYL)-(S)- --.
Column 19, line 35; "(N'T-" should read -- (N'$^{\tau}$- --.
Column 24, line 45; "Maloney" should read -- Moloney --.
Column 25, line 5; "200 pl" should read -- 200 1 --.
Column 25, line 32; "m," should read -- M, --.
Column 25, approximately line 52; "ug/ml," should read -- $\mu$g/ml, --.
Column 26, line 29; "2yl" should read -- 2-yl --.

UNITED STATES PATENT AND TRADEMARK OFFICE
CERTIFICATE OF CORRECTION

PATENT NO. : 5,266,576

DATED : November 30, 1993

INVENTOR(S) : MICHEL VINCENT, GEORGES REMOND, BERNARD PORTEVIN, JEAN-ALBERT BOUTIN, GHANEM ATASSI

It is certified that error appears in the above-indentified patent and that said Letters Patent is hereby corrected as shown below:

Column 26, line 38, 39; "alkyl, $R_3$ represents" should read -- alkyl, and $R_3$ represents --. (PA 2-10-92)

Column 26, line 64; "1" should read -- $\underline{\underline{1}}$ --.

Column 26, line 65; "atoms inclusive" should read -- atoms, inclusive --. (P. 41, ln. 13-PA 2-10-92, P.1)

Column 27, line 20; delete "PH(O" leaving -- $R_5$' being OH or alkoxy, --.

Column 27, line 21; "2" should read -- $\underline{\underline{2}}$ --.

UNITED STATES PATENT AND TRADEMARK OFFICE
CERTIFICATE OF CORRECTION

PATENT NO. : 5,266,576

DATED : November 30, 1993

INVENTOR(S) : Michel Vincent, Georges Remond, Bernard Portevin, Jean-Albert Boutin, Ghanem Atassi It is certified that error appears in the above-indentified patent and that said Letters Patent is hereby corrected as shown below:

```
Column 27, approximately line 24; inclusive which" should read
     -- inclusive, which --. (Cl. 1, PA, P. 2,)
Column 28, line 6; "pharmaceutically acceptable-acid" should
     read -- pharmaceutically-acceptable acid --(Cl. 1,PA, P.2)
Column 28, line 10; "pharmaceutically acceptable-" should read
     --pharmaceutically-acceptable- --. (Cl. 2, old Cl. 5,
     PA, P. 3)
```

Signed and Sealed this

Eighteenth Day of October, 1994

Attest:

BRUCE LEHMAN

Attesting Officer     Commissioner of Patents and Trademarks